United States Patent
Zhang et al.

(10) Patent No.: US 12,343,149 B2
(45) Date of Patent: Jul. 1, 2025

(54) SYSTEM FOR CLASSIFYING WORKING MEMORY TASK MAGNETOENCEPHALOGRAPHY BASED ON MACHINE LEARNING

(71) Applicant: ZHEJIANG LAB, Hangzhou (CN)

(72) Inventors: Yu Zhang, Hangzhou (CN); Haotian Qian, Hangzhou (CN); Chaoliang Sun, Hangzhou (CN); Zhichao Wang, Hangzhou (CN); Huan Zhang, Hangzhou (CN); Tianzi Jiang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/798,861

(22) Filed: Aug. 9, 2024

(65) Prior Publication Data
US 2024/0398305 A1    Dec. 5, 2024

Related U.S. Application Data

(63) Continuation of application No. PCT/CN2023/124641, filed on Oct. 16, 2023.

(30) Foreign Application Priority Data

Oct. 19, 2022   (CN) .......................... 202211276176.0

(51) Int. Cl.
*A61B 5/245* (2021.01)
*A61B 5/00* (2006.01)

(52) U.S. Cl.
CPC ............ *A61B 5/245* (2021.01); *A61B 5/4064* (2013.01); *A61B 5/7203* (2013.01); *A61B 5/7221* (2013.01); *A61B 5/7264* (2013.01)

(58) Field of Classification Search
CPC .............................................. A61B 5/245–246
See application file for complete search history.

(56) References Cited

U.S. PATENT DOCUMENTS

2021/0346096 A1    11/2021   He et al.

FOREIGN PATENT DOCUMENTS

| CN | 110393525 A | 11/2019 |
|---|---|---|
| CN | 110604565 A | 12/2019 |

(Continued)

OTHER PUBLICATIONS

Esch et al. "MNE: Software for Acquiring, Processing, and Visualizing MEG/EEG Data" Magnetoencephalography, Springer International Publishing, (2019) pp. 355-371. (Year: 2019).*

(Continued)

*Primary Examiner* — Angela M Hoffa
(74) *Attorney, Agent, or Firm* — Wiersch Law Group

(57) ABSTRACT

A system for classifying working memory task magnetoencephalography based on machine learning, including: the magnetoencephalography data acquisition module configured to acquire magnetoencephalography data of a subject in different working memory task states; the magnetoencephalography data preprocessing module configured to control the quality of magnetoencephalography data in different working memory tasks and separate noises and artifacts; the magnetoencephalography source reconstruction module configured for sensor signal analysis and source reconstruction analysis for the data processed by the magnetoencephalography data preprocessing module; and the machine learning classification module is configured to classify the working memory tasks to which the subjects belong by taking power time series as features. The present disclosure integrates the complete analysis pipeline from preprocessing to source reconstruction of the working memory magneto- (Continued)

encephalography data, classifies the working memory task magnetoencephalography data, and is of great significance to the study of working memory decoding and brain memory related mechanisms.

6 Claims, 2 Drawing Sheets

(56) References Cited

FOREIGN PATENT DOCUMENTS

| CN | 111340142 A | 6/2020 |
|---|---|---|
| CN | 112220485 A | 1/2021 |
| CN | 112446264 A | 3/2021 |
| CN | 113160975 A | 7/2021 |
| CN | 113918008 A | 1/2022 |
| CN | 114052668 A | 2/2022 |
| CN | 114065825 A | 2/2022 |
| CN | 115132349 A | 9/2022 |
| CN | 115359236 A | 11/2022 |
| JP | 2010046335 A | 3/2010 |

OTHER PUBLICATIONS

Jas et al. "MEG/EEG group study with MNE: recommendations, quality assessments and best practices". bioRxiv preprint doi: https://doi.org/10.1101/240044; this version posted Dec. 28, 2017. 30 pages. (Year: 2017).*

Syrjala et al. "Decoding working memory task condition using magnetoencephalography source level long-range phase coupling patterns". J Neural Eng. 18 (2021) 17 pages. (Year: 2021).*

Halder et al. "Quantitative Evaluation in Estimating Sources Underlying Brain Oscillations Using Current Source Density Methods and Beamformer Approaches" ENEURO.0170-19. (2019) 1-14. (Year: 2019).*

Mantini et al. "Improving MEG Source Localization: An Automated Method for Complete Artifact Removal Based on Independent Component Analysis" NeuroImage 40 (2008) 160-173. (Year: 2007).*

MNE Developers. "Getting started with mne.Report" MNE-Python v0.24.1. https://mne.tools/0.24/auto_tutorials/intro/70_report.html Retrieved from the website on Dec. 12, 2024. Published online Dec. 3, 2021. One page. (Year: 2021).*

Mantini et al. "A Signal-Processing Pipeline for Magnetoencephalography Resting-State Networks" Brain Connectivity vol. 1, No. 1, (2011) 49-59. (Year: 2011).*

International Search Report (PCT/CN2023/124641); Date of Mailing: Jan. 9, 2024.

Notice of Allowance(202211276176.0 ); Date of Mailing: Jan. 5, 2023.

Research-on-MEG-Decoding-Based-on-Transfer-Learning.
A-Dissertation-Submitted-to-PLA-Strategic-Support-Force-Information-Engineering-University-for-the-Degree-of-Master-of-Engineering.
Study-of-removal-of-artifacts-in-MEG-using-PCA-and-ICA.
Machine-learning-approaches-for-classification-of-imaginary-movement-type.

* cited by examiner

SYSTEM FOR CLASSIFYING WORKING MEMORY TASK MAGNETOENCEPHALOGRAPHY BASED ON MACHINE LEARNING

CROSS-REFERENCE TO RELATED APPLICATIONS

The present application is a continuation of International Application No. PCT/CN2023/124641, filed on Oct. 16, 2023, which claims priority to Chinese Application No. 202211276176.0, filed on Oct. 19, 2022, the contents of both of which are incorporated herein by reference in their entireties.

TECHNICAL FIELD

The present disclosure relates to the technical field of neuroimaging data analysis and machine learning, and in particular, to a system for classifying working memory task magnetoencephalography based on machine learning.

BACKGROUND

As the most mysterious organ in the human body, the brain is constantly explored by people for its mystery, and people are trying to understand its internal mechanism and working mechanism. In recent years, with the development of functional magnetic resonance imaging (fMRI), Electroencephalogram (EEG), Magnetoencephalography (MEG), Positron Emission Computed Tomography (PET) and other imaging technologies have made new progress in the study of the brain, and these technologies are further playing an increasingly important role in exploring the mechanism of the human brain and related cognitive activities. Among them, exploring the brain with functional imaging techniques such as EEG, fMRI and MEG has become one of the hot topics (He B, Liu Z. Multimodal Functional Neuroimaging: Integrating Functional MRI and EEG/MEG [J]. IEEE reviews in biomedical engineering, 2008, 1(2008): 23-40). Electroencephalogram (EEG) draws an image by collecting the potential difference at different positions on the scalp, which has the advantage of high time resolution and can capture the changes of the brain in a very short time. However, the number of traditional EEG electrodes is limited, the spatial resolution is poor, and the EEG conduction is very different in different media such as brain tissue, cerebrospinal fluid, skull and skin, which makes source reconstruction difficult (Roberta Grech, Cassar Tracey, Muscat Joseph, et al. Review on solving the inverse problem in EEG source analysis [J]. Journal of neuroengineering and rehabilitation, 2008, 5 (1): 25). fMRI is based on the blood oxygenation level dependent (BOLD) of the brain, which reflects the change of deoxyhemoglobin concentration caused by task-induced or spontaneous neurometabolic activities, thus indirectly reflecting the neuronal functional activity of the brain (Ugurbil K. Development of functional imaging in the human brain (fMRI); the University of Minnesota experience [J]. Neuroimage, 2012, 62 (2): 613-619). fMRI has the advantages of high spatial resolution, non-invasive acquisition, etc. However, the temporal resolution of the existing fMRI is generally 2 s, which is still low compared with the rapidly changing brain function, and it is not enough to capture the instantaneous changes in the process of brain for processing different tasks. Magnetoencephalography (MEG) studies brain activities by recording the magnetic field generated by the electrical activity of neurons. It records brain activities directly and non-invasively with a very high time resolution (within milliseconds), and generates a dynamic and informative large-scale representation of brain activities (J Gross. Magnetoencephalography in Cognitive Neuroscience: A Primer [J]. Neuron, 2019, 104 (2): 189-204). It has extremely high spatial resolution (1-3 mm) and temporal resolution (1-2 ms), and the magnetic field is less disturbed by cerebrospinal fluid and skull, with non-invasive and non-radioactive checks, and thus it has its unique advantages in studying brain function. It is of great significance to study human brain functions by using the MEG technology, which is expected to provide new insights for revealing the working mechanism of the brain.

Among them, for the magnetoencephalography technology, it collects the magnetic field distribution around the head of the subject, not the magnetic field distribution inside the brain. The magnetic field signal acquired by magnetoencephalography equipment is formed by the superposition of magnetic fields generated by the activities of all neurons inside the brain. The complex neuron activity is abstracted into a dipole model, and then the process is simulated by mathematical method according to the propagation law of the magnetic field in space, which is the so-called forward problem in magnetoencephalography research. What is inverse to the above process is the inverse problem in magnetoencephalography processing, that is, calculating the internal signals of the brain by a correlation algorithm, which is further called MEG source reconstruction. Because the number of neurons in the brain is much larger than the number of sensors in magnetoencephalography equipment, there will be infinite solutions to the inverse problem, which makes the source reconstruction of MEG uncertain. Therefore, the source reconstruction step of MEG data is the key in MEG data processing (S Baillet. Magnetoencephalography for brain electrophysiology and imaging [J]. Nat Neurosci, 2017, 20(3): 327-339). At present, there is no tool to integrate the pipeline for magnetoencephalography data from preprocessing to sensor signal analysis to source reconstruction, so as to achieve automatic processing of MEG data. The existing methods are all based on lower-level processing scripts, which generally have a single function and can only realize a certain step in MEG data processing pipeline, and meanwhile the process is cumbersome, requiring operators to have certain processing experience.

With the rapid development of artificial intelligence technology, more and more researchers have begun to introduce machine learning technology into the exploration of cognitive neuroscience and brain science (Khosla M, Jamison K, Ngo G H, et al. Machine learning in resting-state fMRI analysis [J]. Magnetic Resonance Imaging, 2019, 64:101-121). In brain science research, the most widely used machine learning methods are classification, regression and clustering. With the improvement of data quality and the continuous development of machine learning research methods, machine learning methods have made outstanding achievements in the research of fMRI and EEG, but there are few related studies in MEG field.

In the early research, in view of the unique high-dimensional features of neuroimaging data, researchers usually adopt unsupervised learning methods to obtain the relevant spatio-temporal data features for exploring the potential explanatory factors in unlabeled data. Commonly used unsupervised learning methods include K-means clustering, hierarchical clustering and autoencoders. These methods are applied to brain science and neuropsychiatric diseases, and the main findings of the study can be roughly divided into the following aspects: (1) the differences between subjects; reflecting the potential spatial pattern in the relevant fluctuations; time dynamic structure in some states. In recent years, the use of supervised learning technology, especially classification technology, for brain image data and individual level prediction classification of subjects has aroused great interest in related fields. The key steps of constructing a classification prediction model include feature extraction and selection, model selection and training, model effect evaluation and so on. In machine learning research on neuroimaging data, how to select high-performance features from complex data and construct a classification prediction model as a biomarker for further research has always been a difficult problem for researchers. If a comprehensive system for neuroimage data processing, feature extraction and machine learning classification prediction model can be constructed, it will play an important role in the related research of brain images such as magnetoencephalography and fMRI, and it will be further of great significance for the study of brain-related neural mechanisms.

SUMMARY

Considering the limitations of the prior art, an object of the present disclosure is to provide a system for classifying working memory task magnetoencephalography based on machine learning, which can carry out a comprehensive pipeline from preprocessing to source reconstruction analysis on magnetoencephalography data, and use a machine learning model to classify the magnetoencephalography data of working memory tasks.

The present disclosure is realized by the following technical solution: a system for classifying working memory task magnetoencephalography based on machine learning includes a magnetoencephalography data acquisition module, a magnetoencephalography data preprocessing module, a magnetoencephalography source reconstruction module and a machine learning classification module.

The magnetoencephalography data acquisition module is configured to acquire magnetoencephalography data of subjects in different working memory task states and input the magnetoencephalography data to a magnetoencephalography data preprocessing module. The magnetoencephalography data preprocessing module is configured to preprocess the magnetoencephalography data in the different working memory task states, and includes a data quality control submodule, a low-quality channel and data segment filtering submodule and a noise and artifact separating submodule;

The data quality control submodule is configured to perform quality check on the magnetoencephalography data in the different working memory task states; the low-quality channel and data segment filtering submodule is configured to filter channels and data segments that do not meet requirements; and the noise and artifact separating submodule is configured for noise removal and artifact identification;

The magnetoencephalography source reconstruction module is configured to perform sensor signal analysis and source-level reconstruction analysis on the magnetoencephalography data in the different working memory task states after passing the magnetoencephalography data preprocessing module to obtain power time series features.

The machine learning classification module is configured to perform dimensional reduction through a principal component analysis method based on the power time series features obtained in the magnetoencephalography source reconstruction module, and finally classify working memory tasks of the subjects by using machine learning models.

Further, the data quality control submodule is configured to preliminarily verify the magnetoencephalography data acquired by the magnetoencephalography data acquisition module and output a document of data quality information.

Further, the data quality information recorded by the data quality control submodule includes: magnetoencephalography sampling frequency, the duration of recorded data, the number of magnetoencephalography (MEG) channels, the number of reference channels, the number of electrocardiogram (ECG) channels, the number of electromyogram (EMG) channels, the number of recorded events and average coil movement.

Further, the low-quality channel and data segment filtering submodule is configured to detect noise channels by checking the signal similarity between each magnetoencephalography channel sensor and its neighboring sensors. Channels and data segments that exhibit correlation below a certain threshold or variance ratios above a specified threshold compared to their neighboring channels will be marked as bad channels and bad data segments, respectively, and will be removed from subsequent analyses.

Further, the noise and artifact separating submodule is configured to extract each independent component by using an independent component analysis method classify the independent component into a brain or noise component, and perform noise removal and artifact identification by thresholding three parameters comprising correlation between independent component signals, correlation between power and time series, and correlation between frequency spectra and by multiple iterations of selecting a highest brain component and a lowest artifact pollution.

Further, the sensor signal analysis in the magnetoencephalography source reconstruction module include time-locking analysis and time-frequency analysis; a relationship of signal frequency changing with time is obtained in the time-frequency analysis; the time-locking analysis is used to obtain a processing process of an event by the brain and obtains activity states before and after the event.

Further, a goal of the source-level reconstruction analysis in the magnetoencephalography source reconstruction module is to reversely calculate a magnetic field change inside the brain by a magnetic field distribution around the head of the subject; and the source reconstruction analysis adopts beamforming technology, and uses a dynamic imaging of coherent sources method or a linearly constrained minimum variance to carry out source reconstruction.

Further, the machine learning model in the machine learning classification module includes a support vector machine model, a logistic regression model or a random forest model.

Compared with the prior art, the present disclosure has the following beneficial effects. In the related art, the magnetoencephalography data are all processed based on the underlying processing script, and the process is complicated and is not completely automatic. Advantageously, owing to the magnetoencephalography data preprocessing module and the magnetoencephalography source reconstruction module, the system in the present disclosure can clearly sort out the scheme of the magnetoencephalography data from preprocessing to sensor signal analysis, and then to source reconstruction, thereby facilitating operation and meeting the needs of automatic analysis. Further, based on the magnetoencephalography power-time series results obtained by the magnetoencephalography data preprocessing module and the magnetoencephalography source reconstruction module, the system of the present disclosure realizes the dimensionality reduction of the extracted features in the machine learning classification module, and constructs a machine learning classification model of the working memory magnetoencephalography data, so that the working memory task category to which the subject belongs can be accurately output according to the input magnetoencephalography data, which plays an important role in the related research of magnetoencephalography and is further of great significance to the research of the neural mechanism related to brain working memory.

BRIEF DESCRIPTION OF DRAWINGS

In order to explain the technical solution of the present disclosure more clearly, the drawings needed in the description of the embodiments will be briefly introduced below. It is obvious that the drawings in the following description are only specific embodiments recorded in this application, and they are not limitations on the protection scope of the present disclosure. For those skilled in the art, without creative labor, of course, some other embodiments and drawings can be obtained according to the following embodiments of the present disclosure and its drawings.

DESCRIPTION OF EMBODIMENTS

In order to make a person skilled in the art better understand the technical solution in this application, the present disclosure will be further explained with the attached drawings. But this is only a part of the embodiment of this application, not the whole embodiment. Based on the specific embodiments described in this application, other embodiments obtained by other people in the field without creative work should fall within the scope of the present disclosure.

Preferred embodiments of the present disclosure are described below with reference to the accompanying drawings.

Figure 1:
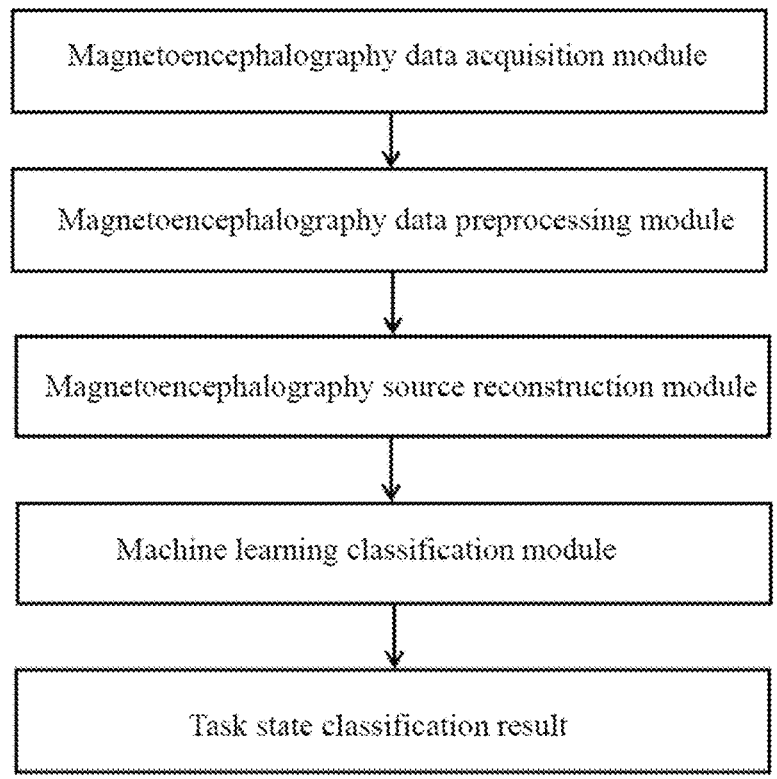
FIG. 1 is a structural diagram of a system for classifying working memory task magnetoencephalography based on machine learning provided by an embodiment of the present disclosure.

Generally, the present disclosure provides a system for classifying working memory task magnetoencephalography based on machine learning, which includes a magnetoencephalography data acquisition module, a magnetoencephalography data preprocessing module, a magnetoencephalography source reconstruction module and a machine learning classification module. This system allows the MEG data from working memory tasks to progress through a comprehensive pipeline, encompassing preprocessing, source reconstruction analysis, and ultimately, classification using a machine learning model. The structure of a working memory task MEG classification system based on machine learning is shown in FIG. 1. An open data set of working memory magnetoencephalography acquired by the magnetoencephalography data acquisition module is input into the system, which firstly passes through the magnetoencephalography data preprocessing module, which is configured for preprocessing the original magnetoencephalography data of different working memory task states, mainly including a data quality control submodule, a low-quality channel and data segment filtering submodule and a noise and artifact separating submodule, so as to control data quality, filter low-quality channels and data segments and separate noises and artifacts by independent component analysis (ICA). Secondly, it passes through the magnetoencephalography source reconstruction module, which is configured for performing sensor-level analysis and source analysis on the data after the magnetoencephalography data preprocessing module to obtain the power-time series. Finally, it passes through the machine learning classification module, the power-time series results obtained in the magnetoencephalography source reconstruction module are used as the original features, and then the original features are reduced in dimension by principal component analysis (PCA). Finally, a machine learning model such as a support vector machine (SVM) is trained for classification. The output is the task state to which the subject belongs. Each module of the system provided by the present disclosure is specifically realized as follows.

The magnetoencephalography data acquisition module was used to collect magnetoencephalography data disclosed in the Human Connectome Project (HCP, link address: https://db.humanconnectome.org/data/projects/HCP_1200). In this project, the magnetoencephalography data of 95 subjects were collected for working memory tasks, and the data of 83 of them were available. The data for working memory of each subject was acquired twice, and each acquisition included 160 classic N-Back (N=0 or 2) working memory tasks. Subjects needed to constantly memorize pictures containing faces and common tools, and judged whether the picture was the same as the previous $N^{th}$ picture. All the data were acquired in the magnetic shielding room by using a whole brain MAGNES 3600 (4D Neuroimaging, San Diego) system located in St. Louis University. The MEG system includes 248 magnetometer channels and 23 reference channels, and the sampling rate is 2034.5101 Hz. ECG, EMG signals were acquired synchronously with MEG, and the contact resistances of all electrodes were controlled within 10 K ohms.

Figure 2:
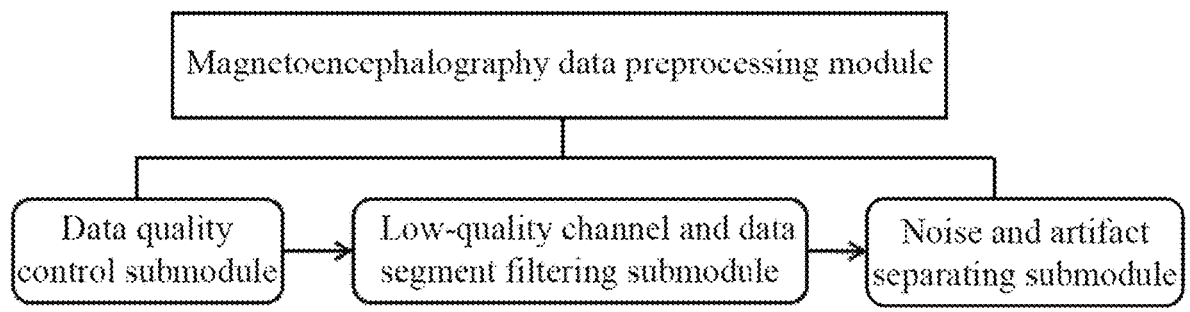
FIG. 2 is a schematic diagram of a magnetoencephalography data preprocessing module provided by an embodiment of the present disclosure.

As shown in FIG. 2, the magnetoencephalography data preprocessing module is used to input the magnetoencephalography data of the HCP into the magnetoencephalography data preprocessing module, which includes a data quality control submodule, a low-quality channel and data segment filtering submodule, and a noise and artifact separating submodule. This embodiment takes the working memory magnetoencephalography data of HCP as an example for illustration.

The data quality control submodule is configured for carrying out preliminary data verification on the magnetoencephalography data acquired by the magnetoencephalography data acquisition module and outputting a document of data quality information; the recorded data quality information includes: magnetoencephalography sampling frequency, the duration of recorded data, the number of MEG channels, the number of reference channels, the number of ECG channels, the number of EMG channels, the number of recorded events and average coil movement.

The low-quality channel and data segment filtering submodule is configured for detecting noise channels by checking the signal similarity between each magnetoencephalography channel sensor and its neighboring sensors, marking the channels that have a correction or a variance ratio with neighboring channels that is lower than a correlation threshold (0.4) or higher than a variance ratio threshold (0.5) as bad channels and bad data segments and removing them from subsequent analyses.

The noise and artifact separating submodule is configured for separating and removing noise and artifacts by using an independent component analysis method. Independent component analysis (ICA) is a blind source separation method, which aims to recover the original independent signal from the mixed observation signal and find a set of linear transformations to make the unmixed signals uncorrelated. In the noise and artifact separating submodule, the independent component analysis method is used to extract each independent component and classify it as brain or noise component. Then, parameters such as the correlation between independent component signals, the correlation between power and time series and the correlation between frequency spectra are thresholded, and noise removal and artifact identification are carried out by multiple iterations of selecting a highest brain component and a lowest artifact pollution. The identified noise components include ECG and eye movement artifacts, power burst and environmental noise.

After passing through the data quality control submodule, low-quality channel and data segment filtering submodule and the noise and artifact separating submodule, the preprocessed HCP working memory magnetoencephalography data is obtained. The trials of these data are divided, and each task state of each subject is divided into several trials. Then, follow-up processing is carried out based on the data split into individual trials.

Figure 3:
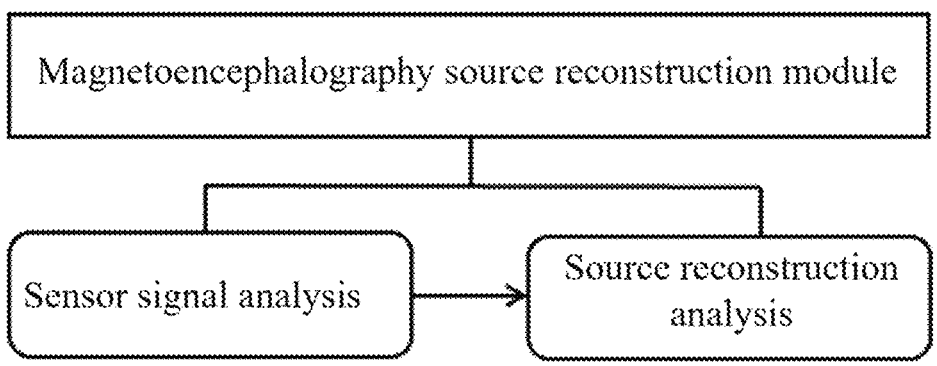
FIG. 3 is a schematic diagram of a magnetoencephalography source reconstruction module provided by an embodiment of the present disclosure.

As shown in FIG. 3, the magnetoencephalography source reconstruction module is used to input HCP data processed by the magnetoencephalography data preprocessing module, which is mainly used for magnetoencephalography data sensor signal analysis and source-level reconstruction analysis. The embodiment of the present disclosure takes the processing pipeline of HCP working memory magnetoencephalography data in the magnetoencephalography source reconstruction module as an example for illustration.

The magnetoencephalography data sensor signal analysis is to directly analyze the signals acquired by the magnetoencephalography sensor and use them as the basis for source reconstruction, which mainly includes two parts: time-locking analysis and time-frequency analysis. Time-frequency analysis method provides joint distribution information of the time domain and frequency domain, which clearly reflects the relationship between signal frequency and time. Time-locking analysis can analyze the brain's processing process of an event, that is, the activity states before and after the event, and is often used to calculate the event-related field (ERF) and covariance matrix.

Referring to the results of sensor signal analysis, the source-level reconstruction analysis is further carried out, with the goal of inversely calculating the magnetic field changes in the brain by using the magnetic field distribution around the subject's head. In source reconstruction, it is necessary to clearly define the relative spatial position between the sensor and the brain and the spatial range of the brain, that is, the so-called head model and the source model. The system of the present disclosure uses MRI data provided by HCP to construct a head model and a source model. The head model is constructed according to the T1-weighted structural MRI image of the subject, and the head model is constructed for each subject with reference to the ft_pre-pareheadmodel function in the FieldTrip toolkit. In the process of constructing the source model, the MRI data of the subject will be registered with a standard template, and the regular grid in the standard space will be inversely transformed by using the transformation matrix obtained from the registration to obtain the source model in the individual space of the subject.

In the process of source reconstruction analysis, the magnetoencephalography source reconstruction module integrates two well-recognized algorithms using beamforming technology, namely, the dynamic imaging of coherent sources (DICS) method and the linearly constrained minimum variance (LCMV) method. The DICS algorithm is based on frequency domain data, and time-frequency analysis is needed to obtain the time-frequency distribution of data before analysis. LCMV, a source reconstruction analysis method, is based on time domain data, and before analysis, time-locking analysis is needed for the data to analyze and calculate the covariance matrix of the data. In the magnetoencephalography source reconstruction module, two routes may be selected: time-frequency analysis-DICS algorithm source reconstruction or time-locking analysis-LCMV algorithm source reconstruction. In order to clearly explain the subsequent process, in the embodiment of the present disclosure, the sensor signal analysis adopts the time-frequency analysis method, and the source reconstruction adopts the DICS algorithm, and finally the power-time series feature results in different frequency bands can be obtained.

The embodiment of the present disclosure takes the results in an alpha frequency band (8-15 Hz) as an example, and for each subject, the power series of N*M could be obtained respectively, where N represents the number of defined time points and M represents the number of cortical vertices. N was defined as 200 in this embodiment, representing 200 time points from −1.5 s to 2.5 s, and each time point had an interval of 0.02 s, which meant that the time point when the subject receives visual stimuli was the time point 0, the trial period from 1.5 s before the time point 0 to 2.5 s after the time point 0 was intercepted, and the data of the 200 time points in this time period were analyzed. In the system of the present disclosure, the cortical space with a 4K resolution provided by the Human Connectome Project was adopted, and the corresponding M of this space represented 8004 vertices.

Figure 4:
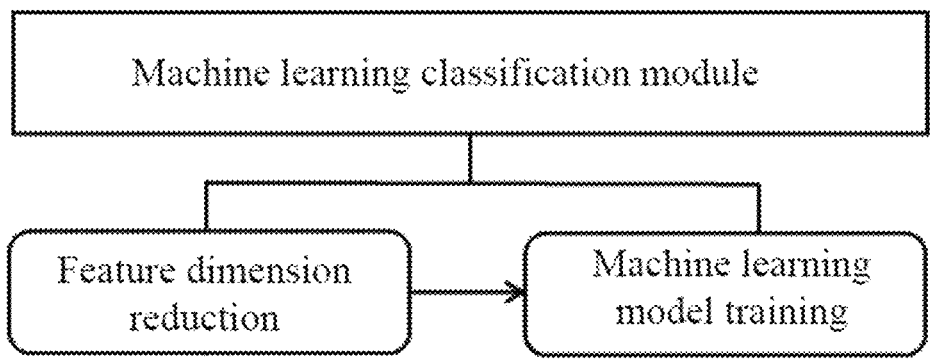
FIG. 4 is a schematic diagram of a machine learning classification module provided by an embodiment of the present disclosure.

As shown in FIG. 4, the machine learning classification module inputs the power-time series feature result data processed by the magnetoencephalography data preprocessing module and the magnetoencephalography source reconstruction module, which is mainly used for feature dimensionality reduction for the power-time series features, and finally trains a variety of machine learning models such as a support vector machine model, a logistic regression model or a random forest model for classification. This embodiment takes HCP magnetoencephalography data as an example, as follows:

Firstly, the power series results of each subject were taken as the feature data set, and dimensionality reduction was carried out on the feature data set by principal component analysis. Principal component analysis (PCA) is often used to reduce the dimension of data sets, while maintaining the features with the most contribution to the variance in the data set. In this embodiment, the specified information was kept to 95% of the original level. Then the data set after dimensionality reduction was randomly divided into a training set, a verification set and a test set according to a ratio of 7:1:2.

Then the data of the training set was input into the machine learning model for training. The adopted machine learning model included a support vector machine model, a logistic regression model or a random forest model, and the data of the verification set was used to optimize the hyper-parameters of the model. The trained machine learning model can output whether the working memory task category belongs to 0-Back or 2-Back. After testing on the data of the test set, the feature data of this example could obtain good classification results in all these three models.

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The above is only the preferred embodiment of this application. This application is not to be limited to the specific embodiments described herein, but is to be covered in the widest scope consistent with the principles and novel features disclosed herein.

What is claimed is:

1. A system for classifying working memory task magnetoencephalography based on machine learning, wherein the system comprises a processor and a memory, and the processor performs following steps:
   acquiring magnetoencephalography data of subjects in different working memory task states and inputting the magnetoencephalography data;
   preprocessing the magnetoencephalography data in the different working memory task states, comprising:
       performing quality check on the magnetoencephalography data in the different working memory task states;
       filtering channels and data segments that do not meet requirements; and
       separating a noise and artifact for noise removal and artifact identification;
   performing sensor signal analysis and source-level reconstruction analysis on the magnetoencephalography data in the different working memory task states to obtain power time series features;
   wherein the sensor signal analysis comprises:
       time-locking analysis: acquiring a processing process of an event by the brain to obtain activity states before and after the event; and
       time-frequency analysis: obtaining a relationship of signal frequency changing with time; and
   wherein the source-level reconstruction analysis comprises: reversely calculating a magnetic field change inside the brain by a magnetic field distribution around a head of the subjects, and adopting a beamforming technology comprising a dynamic imaging of coherent sources method or a linearly constrained minimum variance method, wherein the dynamic imaging of coherent sources method is based on frequency domain data, and performs the time-frequency analysis before the source-level reconstruction analysis to obtain a time-frequency distribution of the magnetoencephalography data; and the linearly constrained minimum variance method is based on time domain data, and performs the time-locking analysis on the magnetoencephalography data before the source-level reconstruction analysis to calculate a covariance matrix of the magnetoencephalography data; and
   performing dimension reduction through a principal component analysis method based on the power time series features, and classifying working memory tasks of the subjects by using a machine learning model.

2. The system for classifying working memory task magnetoencephalography based on machine learning according to claim 1, wherein said performing quality check on the magnetoencephalography data in the different working memory task states further comprises: preliminarily verifying the magnetoencephalography data and outputting a document of data quality information.

3. The system for classifying working memory task magnetoencephalography based on machine learning according to claim 2, wherein the output data quality information comprises: magnetoencephalography sampling frequency, a duration of recorded data, a number of magnetoencephalography (MEG) channels, a number of reference channels, a number of electrocardiogram (ECG) channels, a number of electromyogram (EMG) channels, a number of recorded events and average coil movement.

4. The system for classifying working memory task magnetoencephalography based on machine learning according to claim 1, wherein said filtering channels and data segments that do not meet requirements comprises: detecting noise channels by checking a signal similarity between each magnetoencephalography channel sensor and sensors adjacent to magnetoencephalography channel sensors, and marking channels and data segments, when adjacent channels exhibit lower than a correlation threshold or higher than a variance ratio threshold, as bad channels and bad data segments and removing the bad channels and the bad data segments from subsequent analyses.

5. The system for classifying working memory task magnetoencephalography based on machine learning according to claim 1, wherein said separating a noise and artifact further comprises: extracting each independent component by using an independent component analysis method, classifying the independent component into a brain or noise component, and performing noise removal and artifact identification by thresholding three parameters comprising correlation between independent component signals, correlation between power and time series, and correlation between frequency spectra and by multiple iterations of selecting a highest brain component and a lowest artifact pollution.

6. The system for classifying working memory task magnetoencephalography based on machine learning according to claim 1, wherein the machine learning model consists of a support vector machine model, a logistic regression model or a random forest model.

* * * * *